United States Patent [19]

McDaniel, Jr.

[11] Patent Number: 5,001,114

[45] Date of Patent: Mar. 19, 1991

[54] ALKYL MONO AND POLYGLYCOSIDE PHOSPHATE ESTERS

[75] Inventor: Robert S. McDaniel, Jr., Decatur, Ill.

[73] Assignee: Henkel Kommanditgesellschaft auf Aktien, Duesseldorf, Fed. Rep. of Germany

[21] Appl. No.: 428,463

[22] Filed: Oct. 27, 1989

Related U.S. Application Data

[63] Continuation of Ser. No. 904,144, Sep. 5, 1986, abandoned.

[51] Int. Cl.$^5$ .................... A61K 31/70; C07M 11/04
[52] U.S. Cl. ........................... 514/25; 536/4.1; 536/117; 536/121; 536/123; 514/53; 514/54
[58] Field of Search ................ 536/4.1, 117, 121, 123; 514/25, 53, 54

[56] References Cited

U.S. PATENT DOCUMENTS 4,325,727  4/1982  Vofsi et al. .................... 536/117

FOREIGN PATENT DOCUMENTS 0082793  6/1983  European Pat. Off. ......... 536/4.1
0036693  2/1984  Japan ............................... 536/117
0062599  4/1984  Japan ............................... 536/117

OTHER PUBLICATIONS

*Kirk-Othmer Encyclopedia of Chemical Technology*, 3rd Ed., vol. 22, pp. 359-360, "Sulfated Natural Oils and Fats".
*The Carbohydrates—Chemistry and Biochemistry*, 2d Ed., Edited by Pigman and Horton Academic Press 1972.

Primary Examiner—Johnnie R. Brown
Assistant Examiner—Elli Peselev
Attorney, Agent, or Firm—Ernest G. Szoke; Wayne C. Jaeschke; Daniel S. Ortiz

[57] ABSTRACT

New alkyl mono and polyglycoside phosphate esters and anionic derivatives thereof are described which compounds have the general formula $$RO(G)_xZ_y$$

wherein

G is a glycosyl moiety which is selected from the group consisting of fructose, glucose, mannose, galactose, talose, gulose, allose, altrose, idose, arabinose, xylose, lyxose, ribose or mixtures thereof, R is an aliphatic or aromatic hydrocarbon group substituted on the glycosyl moiety which aliphatic or aromatic group is a straight chain or is branched, or is cyclic, saturated or unsaturated and has 6 to 30 carbon atoms;

$x = 1$ to 10;

$y = 1$ to $3 \times + 1$;

at least one of the hydroxyl groups at the hydroxyl position of at least one of the glycosyl moieties is substituted with Z which is

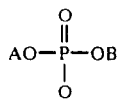

wherein $A = R_1$, $H^+$ or $(G)_xOR$
$B = R_2$, $M^+$ or $(G)_xOR$ except that when B—$R_2$ or $(G)_xOR$, $A \neq H$, when A or $B = (G)_xOR$, Z substitutes one of the hydroxyl groups of the glycosyl moieties of A or B, and $R_1$ and $R_2 =$ an aliphatic or aromatic hydrocarbon group which is a linear straight chain or is branched, open-chain or cyclic, saturated or unsaturated and has 6 to 30 carbon atoms or $CH_3(CH_2)_m(CH_2)_n$, m and $n = 1$ to 27 with $m+n$ greater than or equal to 5 with the total number of carbon atoms in $R_1 + R_2$ not exceeding 50;

$M =$ an organic or inorganic cation.

16 Claims, No Drawings

ALKYL MONO AND POLYGLYCOSIDE PHOSPHATE ESTERS

This application is a continuation of U.S. patent application Ser. No. 06/904,144, filed Sept. 5, 1986 now abandoned.

This invention relates to new alkyl mono and polyglycoside phosphate esters, ionic derivatives of such esters and a method of making such esters and ionic derivatives.

Phosphate esters and alkyl mono and polyglycosides are surface-active agents. The general properties and behavior of surface-active agents are due to the dual character of the molecules of these substances. Their molecules are made up of two parts, a relatively large, elongated part, the hydrophobic group, and a small solubilizing, polar group, the hydrophilic group. The antagonism of these two portions of the molecule and the balance between them gives the compound its surface-active properties. The hydrophilic group exerts a solubilizing effect and tends to draw the entire molecule into solution; the hydrophobic group on the other hand, because of its insolubility, has the effect of resisting this tendency. If a balance between the two groups exists, the substance neither dissolves completely nor remains completely undissolved, but concentrates at an interface such as a liquid-liquid interface or a liquid-solid interface. In a liquid-liquid system which includes an aqueous phase, the molecules of the surface active agent are so oriented that the hydrophilic groups are anchored in the aqueous phase and the hydrophobic groups project into the nonaqueous phase.

Surface-active agents are divided into two broad classes according to their character in water, ionic and nonionic. Compounds belonging the the first class, the ionic surface-active agents, form ions in solution of water or other polar solvents. Compounds of the second class, known as the nonionics, do not ionize, but owe their solubility to the combined effect of a number of weak solubilizing groups such as ether linkages or hydroxyl groups in their molecules.

The ionic class is further subdivided in accordance with the way its members behave upon ionization. If, upon ionization, the ion containing the large hydrophobic group assumes a negative charge and become the anion, the compound is classified as an anionic surface-active agent. In this case the cation will consist of a positively charged ion such as a simple metallic ion such as a sodium or potassium ion or a positively charged radical such as ammonium or alkyl ammonium.

Alkyl polyglycosides are known nonionic surface-active agents which are alkaline and electrolyte stable. They are known to be userful as detergents, gelling agents, lubricants, wetting agents, textile softeners and emulsifiers. U.S. Pat. Nos. 3,598,865; 3,707,535; 3,772,269; 3,839,318 and 4,536,317 all describe such nonionic glycosides. U.S. Pat. Nos. 4,483,787; 4,396,520; and 4,565,647 describe compositions which are mixtures of glycosides and anionic surfactants in an apparent attempt to benefit from the characteristics of the anionic compound.

Alkyl mono and polyglycosides are prepared generally by reacting a monosaccharide, or a compound hydrolyzable to a monosaccharide with an alcohol such as a fatty alcohol in an acid medium. Various glycoside and polyglycoside compounds including alkoxylated glycosides and processes for making them are disclosed in U.S. Pat. Nos. 2,974,134; 3,219,656; 3,598,865; 3,640,998; 3,707,535; 3,772,269; 3,839,318; 3,974,138; 4,223,129 and 4,528,106. All of the latter patents are incorporated by reference herein.

In most cases excess alcohol from the preparation of the glycosides adversely affects the surface active properties of the glycoside and/or makes the glycoside cloudy. Hence, it is desirable to remove the alcohol from the glycoside prior to its use as a surface active agent.

Mono and diesters of orthophosphoric acid are known. These esters and their salts are known to be useful as surface active agents or surfactants including anionic surfactants. Such esters and their salts have been especially useful in emulsion polymerization, laundry compositions such as dry-cleaning compositions where solubility in hydrocarbon solvents is important, industrial and institutional cleaners where alkaline stability and a tolerance for high concentrations of electrolytes are important, pre-spotters, pre-soaks and carpet shampoos.

It is an object of this invention to provide new alkyl mono and polyglycoside phosphate esters and anionic derivatives thereof.

It is another object of this invention to provide compounds which are glycosides with phosphate linkages which linkages have alkaline and electrolyte stability which complements such stability of glycosides.

It is another object of this invention to provide new surface active agents and anionic derivatives thereof through the utilization of alcohols used in the preparation of mono and polyglycosides.

It is yet another object of this invention to provide new surface active agents and a method of making such agents.

These and other objects of the invention will become apparent from the following description.

According to the invention new compounds which are alkyl mono and polyglycoside phosphate esters have been discovered which compounds have the general formula

wherein
G is a glycosyl moiety which is selected from the group consisting of fructose, glucose, mannose, galactose, talose, gulose, allose, altrose, idose, arabinose, xylose, lyxose, ribose, or mixtures thereof,
R is an aliphatic or aromatic hydrocarbon group substituted on the glycosyl moiety which aliphatic or aromatic group is a linear straight chain or is branched, open-chain or cyclic, saturated or unsaturated and has 6 to 30 carbon atoms;
$x = 1$ to $10$
$y = 1$ to $3x+1$
at least one of the hydroxyl groups at the hydroxyl position of at least one of the glycosyl moieties is substituted with Z which is

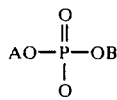

wherein
$A = R_1$, $H^+$ or $(G)_xOR$
$B = R_2$, $M^+$ or $(G)_xOR$ except that when $B=R_2$ or $(G)_xOR$, $A \neq H$, when A or $B=(G)_xOR$, Z substitutes one of the hydroxyl groups of the glycosyl moieties of A or B, and $R_1$ and $R_2$ = an aliphatic or aromatic hydrocarbon group which is a linear straight chain or is branched, open-chain or cyclic, saturated or unsaturated and has 6 to 30 carbon atoms or $CH_3(CH_2)_mO(CH_2)_n$, m and n=1 to 27 with m+n greater than or equal to 5 with the total number of carbon atoms in $R_1+R_2$ not exceeding 50; M—an organic or inorganic cation such as an alkali metal, ammonium, monoethanol-ammonium or calcium; and no more than three

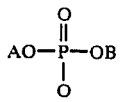

groups are associated with any one glycosyl moiety.

Preferably in the invention, R is an alkyl group which is either straight chain or branched. And when A or B is $R_1$ or $R_2$ respectively, $R_1$ and $R_2$ also are preferably an alkyl group which is a straight chain or branched. The mixture of mono and polyglycoside phosphate esters of the invention are prepared by reacting an alcohol/aliphatic or aromatic mono and polyglycoside mixture with a phosphorylating agent such as $P_2O_5$, $POCl_3$ and $PCl_3$ followed by neutralization with a suitable base such as 50% sodium hydroxide. Generally M is an alkali metal ion such as sodium, potassium or lithium. The base provides the monovalent ion which generally is $Na^+$, $K^+$ or $Li^+$. Sufficient alcohol should be employed to give a fluid reaction product at about 40° to about 80° C. The resulting product is a mixture of products based upon the starting ingredient of both mono and polyglycosides. The resulting product includes mono, di and tri phosphate esters as generally described in the above general formula. The preparation advantageously utilizes alcohols commonly existent in glycoside mixtures after their preparation from saccharides. Moreover, with the preparation of the monovalent salts according to the invention, the invention provides anionic surfactants under mild reaction conditions relative to the reaction conditions required for sulfating or sulfonating reactions. The mild conditions avoid degradation of the glycosyl moieties which form part of the phosphate esters. The final products are normally aqueous solutions of alkyl glycoside phosphate ester mixtures.

One of the most common of the glycosides forming a part of the phosphate esters of the invention are alkyl glucosides, wherein G in the above formula is glucose. The degree of polymerization of polyglycosides in phosphate esters of the invention varies and is in the range of about 1 to 10, i.e., x=1 to 10, the polyglycosides usually existing as mixtures of glycosides of varying degrees of polymerization. Polyglycosides in these mixtures have a degree of polymerization as high as 10, but most of the polyglycosides in the mixtures have a degree of polymerization of 5 or less. Because the glycosides are often found as mixtures, x may be expressed as an average degree of polymerization which includes fractional number. Recognizing that the glycosides, according to the invention, are mixtures of glycosides with varying degrees of polymerization, the average degree of polymerization of the polyglycosides of the invention is from about 1.1 to about 5, preferably 3 or less. R generally is at the $C_1$ position of the glycoside and in most applications of the surface-active agents of this invention, R is an alkyl group which is straight chain or branched having 8 to 18 carbon atoms. And when A or B is $R_1$ or $R_2$ respectively, $R_1$ and $R_2$ in most applications of the invention are alkyl groups having 8 to 18 carbon atoms.

The alcohols which may be reacted with the glycosides and phosphorylating agent include alkyl alcohols which are straight or branched having 6 to 30 carbon atoms or alkoxy alcohols having from about 6 to about 30 carbon atoms, with the alcohol in most surface active applications for the resulting phosphate ester having 8 to 18 carbon atoms, the alkyl or alkoxy portion of the alcohol most commonly corresponding to the aglycone groups of the glycoside. Although not required, the alkyl or alkoxy groups of the alcohol commonly and conveniently correspond to the aglycon groups of the glycosides because the excess alcohols used in the glycosidation reaction in preparation of the glycosides may be used in the preparation of the phosphate esters with the phosphorylating agent. As a result special solvents such as N,N-dimethylformamide, dimethyl sulfoxide or hydrocarbons are not required in reacting the glycoside, phosphorylating agent and alcohol.

The number of Z substituents (y) may be as many as $3x+1$. The number of phosphate linkages on a glycosyl moiety, however, generally is limited by the amount of charging created by the ionic repulsion created by putting multiple anionic groups on one glycosyl, the molar ratio of phosphorylating agent to alkyl glycoside, and stearic considerations including the position at which the glycosyl moieties are bonded to one another. For example, if the glycosyl group is a six-membered ring, it is more likely that if the rings are bonded at the 1, 4, or 1, 3 positions, two or three phosphate ester linkages can be made more easily onto the glycosyl ring than if the rings were bonded by linkages at the 1, 6 or 1, 2 positions of the glycosyl rings. In the latter use, it is more likely that one phosphate ester linkage will be on each glycosyl moiety. On average, even though y may be $3x+1$, the extent of phosphate substitution (y) on the glycosyl moiety of the compounds of the invention is less than about 2 and usually about 1 per glycosyl moiety.

Examples of the compounds of the invention were made as follows.

EXAMPLE I

Preparation of phosphate surfactant mixture:

$C_{12}H_{25}O(G)_xOPO_3HK$;

$(C_{12}H_{25}O(G)_xO)_2PO_2K$;

$(C_{12}H_{25}O(G)_xO)_3PO$;

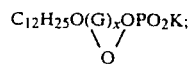
$C_{12}H_{25}O(G)_xOPO_2K$;
    \\ /
     O

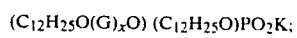
$(C_{12}H_{25}O(G)_xO)(C_{12}H_{25}O)PO_2K$;

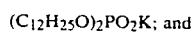
$(C_{12}H_{25}O)_2PO_2K$; and

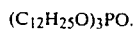
$(C_{12}H_{25}O)_3PO$.

0.25 moles of dodecyl glycoside having an average degree of polymerization of 1.2 is dissolved in 270 mls of dodecyl alcohol in a 500 ml, three necked round bottom flask equipped with an overhead stirrer and immersed in a 45° C. constant temperature bath. When the solution warms to 40° C., phosphorous pentoxide, 68 g, is added slowly to maintain a reaction temperature of 50° C. +/−5° C. Heating and stirring are maintained for 15 minutes after dissolution of the phosphorous pentoxide. Then the reaction product is neutralized with 108 g of 50% aqueous potassium hydroxide. (Note: 101 g of diethanolamine can be used instead of the aqueous potassium hydroxide.) After neutralization, the product is then diluted with water to a useful concentration (typically less than 50% solids). This diluted product can be used as is or bleached and/or decolorized by standard methods. The composition of the reaction product is substantially as claimed.

It should be understood that while certain preferred embodiments of the present invention have been illustrated and described, various modifications thereof will become apparent to those skilled in the art. Accordingly, the scope of the present invention should be defined by the appended claims and equivalents thereof.

Various features are set forth in the following claims. What is claimed is:

1. A composition containing a mixture comprising compounds of the formula $RO(G)_xZ_y$ wherein
G is a glycosyl moiety selected from the group consisting of fructose, glucose, mannose, galactose, talose, gulose, allose, altrose, idose, arabinose, xylose, lyxose, ribose or mixtures thereof,
R is an aliphatic, cyclic or aromatic hydrocarbon group, each having from 6 to 30 carbon atoms, substituted on the glycosyl moiety, the aliphatic group is straight chain or, branched, the aliphatic or cyclic group is a saturated or unsaturated group;
x is a number from 1 to 10;
y is a number from 1 to 2x;
at least one of the hydroxyl groups of at least one of the glycosyl moieties is substituted with Z which is

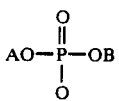

A is $R_1$, $H^+$ or $(G)_xOR$,
B is $R_2$, $M^+$ or $(G)_xOR$,
except that when B is $R_2$ or $(G)_xOR$, A is not $H^+$, when A or B is (G)OR, Z substitutes one of the hydroxyl groups of the glycosyl moieties of A or B, and $R_1$ and $R_2$ are aliphatic, cyclic or aromatic hydrocarbon groups having from 6 to 30 carbon atoms, the aliphatic group is linear or, branched, the aliphatic or cyclic group is saturated or unsaturated with the total number of carbon atoms in $R_1 + R_2$ not exceeding 50; $M^+$ is an organic or inorganic cation.

2. A composition of claim 1 wherein $R_1$, and $R_2$ are alkyl groups which are straight chains or branched and no more than three

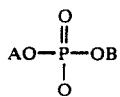

groups are associated with anyone glycosol group, wherein
A is $R_1$, $H^+$ or $(G)_xOR$;
B is $R_2$, $M^+$ or $(G)_xOR$; R is a straight chain or branched chain, a saturated or unsaturated aliphatic group having from 6 to 30 carbon atoms, a saturated or unsaturated cyclic group having from 6 to 30 carbon atoms, or an aromatic hydrocarbon group having from 6 to 30 carbon atoms, substituted on the glycosol moiety; x is a number from 1 to 10; y is a number from 1 to 2 x; and $R_1$ and $R_2$, are independently selected linear or branched, saturated or unsaturated aliphatic hydrocarbon groups having from 6 to 30 carbon atoms, saturated or unsaturated cyclic hydrocarbon groups having from 6 to 30 carbon atoms, aromatic hydrocarbon groups having from 6 to 30 carbon atoms with the total number of carbon atoms in $R_1$ plus $R_2$ not exceeding 50; $M^+$ is an organic or inorganic cation.

3. A composition of claim 2 wherein G is glucose and $M^+$ is selected from the group consisting of $Na^+$, $K^+$ or $Li^+$.

4. A composition of claim 2 wherein the glycosyl groups have an average degree of polymerization, x, in the range of about 1.1 to about 5.

5. A composition of claim 2 wherein R is an alkyl group which is straight chain or branched having 8 to 18 carbon atoms.

6. A composition of claim 2 of the formula $RO(G)_xZ_y$ wherein G is a glycosyl moiety selected from the group consisting of fructose, glucose, mannose, galactose, talose, qulose, allose, altrose, idose, arabinose, xylose, lyxose or mixtures thereof;
x is a number from 1 to 10;
y is a number less than about 2x;
at least one of the hydroxyl groups of at least one of the glycosyl moieties is substituted with Z which is

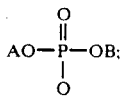

wherein;
A is $R_1$, $H^+$ or $(G)_xOR$;
B is $R_2$, $M^+$ or $(G)_xOR$;
except that when B is $R_2$ or $(G)_xOR$, A is not $H^+$, when A or B is $(G)_xOR$, Z substitutes one of the hydroxyl groups of the glycosyl moieties of A or B, and wherein $R_1$ and $R_2$ are independently selected alkyl groups which are straight chain or branched having from 6 to 30 carbon atoms and no more than three

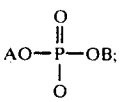

groups are associated with any one glycosyl moiety.

7. A composition of claim 3 wherein x is in the range of about 1.1 to about 5.

8. A composition of claim 7 wherein R is an alkyl group which is straight chain or branched having 8 to 18 carbon atoms.

9. A composition of claim 8 of the formula

RO(G)$_x$Z$_y$ wherein
G is a glucosyl moiety;
x is 1.1 to 5;
y is from 1 to less than 2X;
R is an alkyl group, straight chain or branched having 8 to 18 carbon atoms, and RO is substituted on the C$_1$ carbon of the glucosyl moiety;
Z is $$AO-\overset{\overset{O}{\|}}{\underset{O}{P}}-OB;$$

wherein A is R$_1$, H$^+$ or (G)$_x$OR; B is R$_2$, M$^+$ or (G)$_x$OR; except that when B is R$_2$ or (G)$_x$OR, A is not H$^+$, when A or B is (G)$_x$OR Z substitutes one of the hydroxyl groups of the glucosyl moieties of A or B, and R$_1$ and R$_2$ are independently alkyl groups which are straight chain or branched having from 8 to 18 carbon atoms and M$^+$ is at least one member selected from the group consisting of Na$^+$, K$^+$ or Li$^+$.

10. A composition of claim 8 wherein A is H$^+$ and B is at least one cation selected from the group consisting of Na$^+$, K$^+$ and Li$^+$.

11. A composition of claim 8 wherein A is R$_2$ which is an alkyl group which is straight chain or branched having 8 to 18 carbon atoms and B is at least one cation selected from the group consisting of Na$^+$, K$^+$ and Li$^+$.

12. A composition of claim 8 wherein A or B is (G)$_x$OR wherein G is a glucosyl moiety, R is a straight chain or branched chain alkyl group having from 8 to 18 carbon atoms attached to the glucosyl moiety through the oxygen at the C$_1$ position and x is a number of from 1.1 to 5.

13. A composition of claim 10 wherein y is less than about x and x is a number from 1 to 10.

14. A composition of claim 11 wherein y is less than about x and x is a number from 1 to 10.

15. A composition of claim 12 wherein y is less than about x and x is a number from 1 to 10.

16. A composition of claim 1 wherein the organic or inorganic cation is at least one moiety selected the group consisting of alkali metal, ammonium, calcium and monoethanol ammonium.

* * * * *